(12) United States Patent
Helt, III et al.

(10) Patent No.: US 8,308,666 B2
(45) Date of Patent: Nov. 13, 2012

(54) NEUROMUSCULAR THERAPEUTIC DEVICE

(75) Inventors: Donald G. Helt, III, Old Bridge, NJ (US); Daniel Weber, Middletown, NJ (US); Peter M. Sanzio, Lincroft, NJ (US)

(73) Assignee: LaProxima Technologies, Inc., Old Bridge, NJ (US)

( * ) Notice: Subject to any disclaimer, the term of this patent is extended or adjusted under 35 U.S.C. 154(b) by 1197 days.

(21) Appl. No.: 12/133,054

(22) Filed: Jun. 4, 2008

(65) Prior Publication Data

US 2008/0300519 A1    Dec. 4, 2008

Related U.S. Application Data

(60) Provisional application No. 60/941,750, filed on Jun. 4, 2007.

(51) Int. Cl.
*A61H 1/00* (2006.01)
(52) U.S. Cl. .......................................... 601/46; 601/47
(58) Field of Classification Search .................... 84/705; 381/62; 601/46, 47
See application file for complete search history.

(56) References Cited

U.S. PATENT DOCUMENTS

| 3,699,233 | A | * | 10/1972 | Suzuki | 84/705 |
| 3,795,756 | A | * | 3/1974 | Suzuki | 84/705 |
| 4,308,422 | A | * | 12/1981 | Schmoll, III | 381/62 |
| 4,308,428 | A | * | 12/1981 | Finch | 381/62 |
| 5,101,810 | A | | 4/1992 | Skille et al. | |

* cited by examiner

*Primary Examiner* — Michael A. Brown
(74) *Attorney, Agent, or Firm* — Wall & Tong, LLP

(57) ABSTRACT

Apparatus and method for delivering audible, electrical or mechanical tones having a specific characteristic to a human vestibular system to achieve thereby a therapeutic result.

17 Claims, 5 Drawing Sheets

NEUROMUSCULAR THERAPEUTIC DEVICE

CROSS-REFERENCE TO RELATED APPLICATIONS

This application claims the benefit of U.S. provisional patent application Ser. No. 60/941,750 filed on Jun. 4, 2007 which application is incorporated herein by reference.

FIELD OF THE INVENTION

The present invention relates to a device and method for delivering audible, electrical or mechanical tones to a human vestibular system to achieve thereby a therapeutic result.

BACKGROUND

The United States National Library of Medicine defines muscle tone as "the state of activity or tension of a muscle beyond that related to its physical properties, that is, its active resistance to stretch." Muscle tone is what enables an individual to move or maintain a specific posture. Individuals whose muscles are in a hypertonic or hypotonic state such as, respectively, spastic cerebral palsy patients or astronauts, have extreme difficulty controlling various muscle groups and are in need of alternative therapeutic modalities. Current clinical practices address these issues either pharmacologically or surgically, but provide less than desirable results. Less invasive modalities delivering longer periods of altered muscle tone are needed most when addressing quality of life issues and rehabilitative success.

It is known that the human vestibular system provides a peripheral sensory function and resultant motor information for the brain. Specifically, two otoliths per ear sense linear accelerations; namely the Utricle, which senses horizontal, earth-horizontal linear accelerations and static head tilt, and the Saccule, which senses vertical acceleration. In addition, three semicircular canals sense angular accelerations. The motor output of the vestibular system (the Vestibulo-Spinal Reflex (VSR)) drives skeletal muscles such as anti-gravity muscles (extensors of the neck, trunk, and extremities), stabilizes head, and controls erect stance relative to gravity (push-pull mechanism).

BRIEF SUMMARY

Various deficiencies of the prior art are addressed by the present invention of a method and system in which infrasonic and/or near-infrasonic frequencies are adapted using various frequency and amplitude modulations to produce a signal that is employed to provide neuromuscular reconditioning, testing and/or other therapeutic functions.

In one embodiment, a method for treating a neuromuscular condition comprises: generating a first signal having an approximate frequency between 4 Hz and 90 Hz; frequency modulating the first signal in accordance with a second signal having an approximate frequency between 20 Hz and 60 Hz; and amplitude modulating the frequency modulated signal produce a signal adapted to stimulate vestibular end-organs in a human.

BRIEF DESCRIPTION OF THE DRAWINGS

The teachings of the present invention can be readily understood by considering the following detailed description in conjunction with the accompanying drawings, in which.

To facilitate understanding, identical reference numerals have been used, where possible, to designate identical elements that are common to the figures.

DETAILED DESCRIPTION OF THE INVENTION

In recent years acoustic stimulation has been employed as a tool to quantify dysfunction of the vestibular system, modify its performance, and alter muscular condition. Current research provides strong evidence that acoustic stimuli delivered both monaurally and binaurally to an individual's ears affects the condition of antigravity muscles via the otolith organs. The invention targets these otolith organs, specifically the saccule, which science agrees quantifies vertical accelerations of the body and has been shown to be the most sound-sensitive vestibular end-organ.

The invention will be primarily described within the context of a neuromuscular therapeutic device and related methodology used to raise or lower muscular tonus in hypo and hyper tonic patients. The device employs infrasonic and/or near infrasonic tones that are modulated in both amplitude and frequency to stimulate the vestibular end-organs of a patient to cause thereby habituation of neuromuscular impulses to the so-called antigravity/postural muscles. Vestibular evoked myogenic potentials (VEMP), the vestibular ocular reflex (VOR), the vestibulo-spinal reflex (VSR), and vibroacoustic therapy are four subject areas complimenting the clinical objectives of this device.

Various embodiments include a stand-alone handheld device, a computer controlled application and a vestibular implant device. As a biomedical device used therapeutically, apparatus according to the invention addresses these issues by noninvasively stimulating vestibular end-organs in such a manner that alters muscle tonus. As a general consumer product, apparatus according to the invention can be used daily simply as a relaxation device. The apparatus according to the invention could also be used in vestibular system rehabilitation and neuromuscular reeducation.

Figure 1:
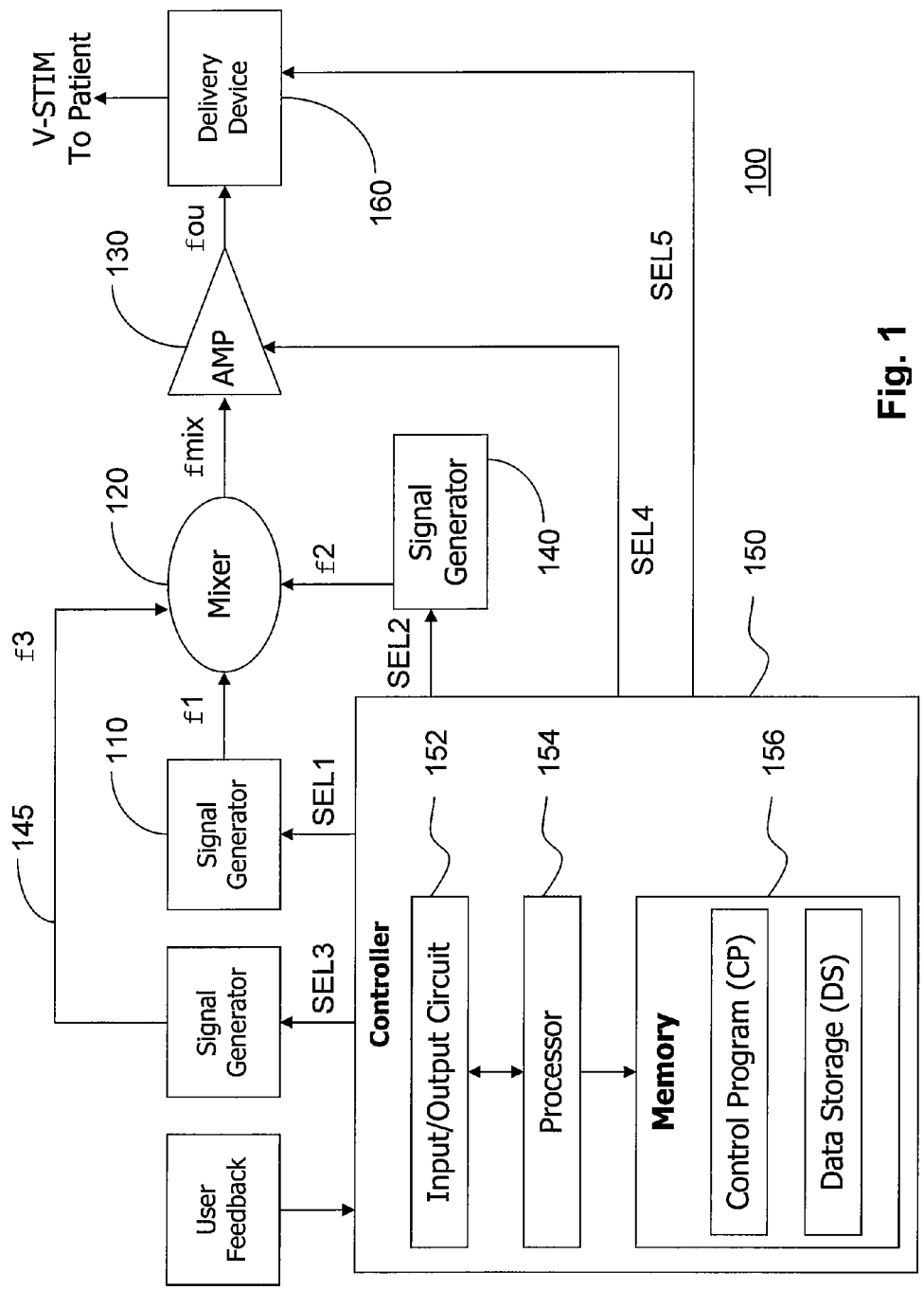
FIG. 1 depicts a high-level block diagram of an apparatus according to one embodiment.

FIG. 1 depicts a high-level block diagram of an apparatus according to one embodiment. Specifically, the apparatus 100 of FIG. 1 includes a first signal generator 110, a mixer 120, an amplifier 130, a second signal generator 140, a controller 150 and a delivery device 160.

The first signal generator 110 operates to produce an output signal $f_1$ in response to, optionally, a frequency selection control signal $SEL_1$ provided by the controller 150. The output signal $f_1$ comprises an oscillating electrical signal having an infrasonic or near infrasonic frequency, illustratively a frequency between 4 and 90 Hz. The output signal $f_1$ is coupled to a first input of the mixer 120.

The second signal generator 140 operates to produce an output signal $f_2$ in response to, optionally, a frequency selection control signal $SEL_2$ provided by the controller 150. The output signal $f_2$ comprises an oscillating electrical signal having a frequency between, illustratively, 20 and 60 Hz. The output signal $f_2$ is coupled to a second input of the mixer 120.

The third signal generator 145 operates to produce an output signal $f_3$ in response to, optionally, a frequency selection control signal $SEL_3$ provided by the controller 150. The output signal $f_3$ comprises an oscillating electrical signal having a frequency between, illustratively, 0.1 and 2.0 Hz. The output signal $f_3$ is coupled to a third input of the mixer 120.

The mixer 120 operates to mix the first $f_1$, second $f_2$ and third $f_3$ signal generator output signals to produce a mixed output signal $f_{mix}$, which is coupled to the amplifier 130.

The amplifier 130 operates to amplify the mixed output signal $f_{mix}$ in response to, optionally, a control signal $SEL_4$ provided by the controller 150. The amplifier output signal $f_{out}$ is coupled to a second input of the mixer 120. The amplifier output signal $f_{out}$ comprises an electrical signal having associated with spectral and amplitude characteristics adapted to stimulate vestibular end-organs of a patient to cause thereby habituation of neuromuscular impulses to the so-called antigravity/postural muscles.

The delivery device 160 converts the amplifier output signal $f_{out}$ as necessary to produce a vestibular stimulation signal V-STIM for use by a patient or subject. Specifically, in an audio embodiment, the vestibular stimulation signal V-STIM comprises an audio signal such that the delivery device 160 comprises audio speakers or and audio delivery system such as a personal audio device (e.g., an MP3 player, ipod and the like). In an implant embodiment, the vestibular stimulation signal V-STIM comprises an electrical signal used to stimulate an implanted device within one or both of a patient's ears. Operating parameters of the delivery device are optionally controlled via the controller using a control signal $SEL_5$.

It should be noted that elements depicted as adjustable and/or controlled may also be implemented in a fixed manner. For example, the various signals that are depicted as adjustable via control of a corresponding signal generator may optionally be implemented by a fixed (nonadjustable) signal generator.

The controller 150 includes input/output circuitry 152, processor circuitry 154 and memory 156. The memory 156 includes a control program CP and a data storage DS. The control program CP is executed via the processor 154 to perform the various steps and implement the various methodologies discussed herein with respect to the present invention. The controller 150 operates as a computing device to generate the control signals used by the first signal generator 110, second signal generator 140, amplifier 130 and/or delivery device 160. In this manner, the controller 150 controls the initial or base signal provided by the first signal generator 110, controls the frequency modulation signal provided by signal generator 140, controls the amplitude modulation provided by amplifier 130, and/or control operating parameters (e.g., audio volume, electrical intensity, mechanical vibration intensity etc.) of the delivery device 160.

The controller 150 also response to a user feedback signal to adjust any or all of the various control signals. For example, in various embodiment a user may control one or more of the first $f_1$, second $f_2$ and third $f_3$ signals, the amplitude modulation and various parameters associated with the delivery device (e.g., volume, mechanical intensity, electrical intensity and so on. this manner, a user or patient receiving a therapeutic treatment may adapt the spectral and/or amplitude components associated with signal delivering the therapeutic treatment. In this manner, characteristics of a V-STIM signal delivered to a patient may be adapted to compensate for physical differences between patients. That is, some patients may require higher or lower spectral modulation and/or amplitude modulation to achieve the desired therapeutic effect.

In one embodiment of the invention, the V-STIM signal delivered to a patient includes other audio signals such as music, natural sounds (e.g., ocean waves and the like) and so on. In effect, the V-STIM signal is masked by the other audio signals such that soothing effects of the other audio signals in conjunction with the V-STIM signal provide a more relaxing experience.

In one embodiment of the invention, circuitry adapted to providing appropriate signals to a patient is included within a device implanted within a patient. For example, within the context of treatment for cerebral palsy, such an implanted device providing a V-STIM signal for some portion or the entirety of the day operates to relax the patient's muscles and improve the patient quality of life.

Generally speaking, the V-STIM signal need only convey the spectral/amplitude qualities adapted to stimulate the vestibular system. The V-STIM signal may be electrical, audible or mechanical in nature. An audio V-STIM signal is conveyed by a delivery device including audio speakers. A mechanical V-STIM signal is conveyed by a delivery device (e.g., vibratory apparatus) in mechanical contact with the skull or a bony protrusion proximate the vestibular system. This may be accomplished by a vibratory apparatus attached to, or otherwise in mechanical communications with the mastoid process. Alternately, vibratory apparatus may be attached to, or in mechanical communication with the whole body (whole body vertical oscillation) or any other mechanical communication technique suitable for stimulating the vestibular system (e.g., the saccule). An electrical/electromechanical V-STIM signal is conveyed by an implanted or external delivery device adapted for delivering frequency and amplitude appropriate perturbations to the vestibular system.

It will be appreciated by those skilled in the art that while a single mixer is depicted, additional mixers may be utilized in sequence to achieve the described mixing function. Moreover, while the third frequency $f_3$ is depicted as being provided by a third signal generator 145, this frequency may be provided directly from the controller 150 or from some other source. Generally speaking, each of the frequencies generated to by the various signal generators may be provided alternatively by the controller 150. In one embodiment, a single complex signal generator is used which provides at its output the desired signal $f_{mix}$.

Figure 2:
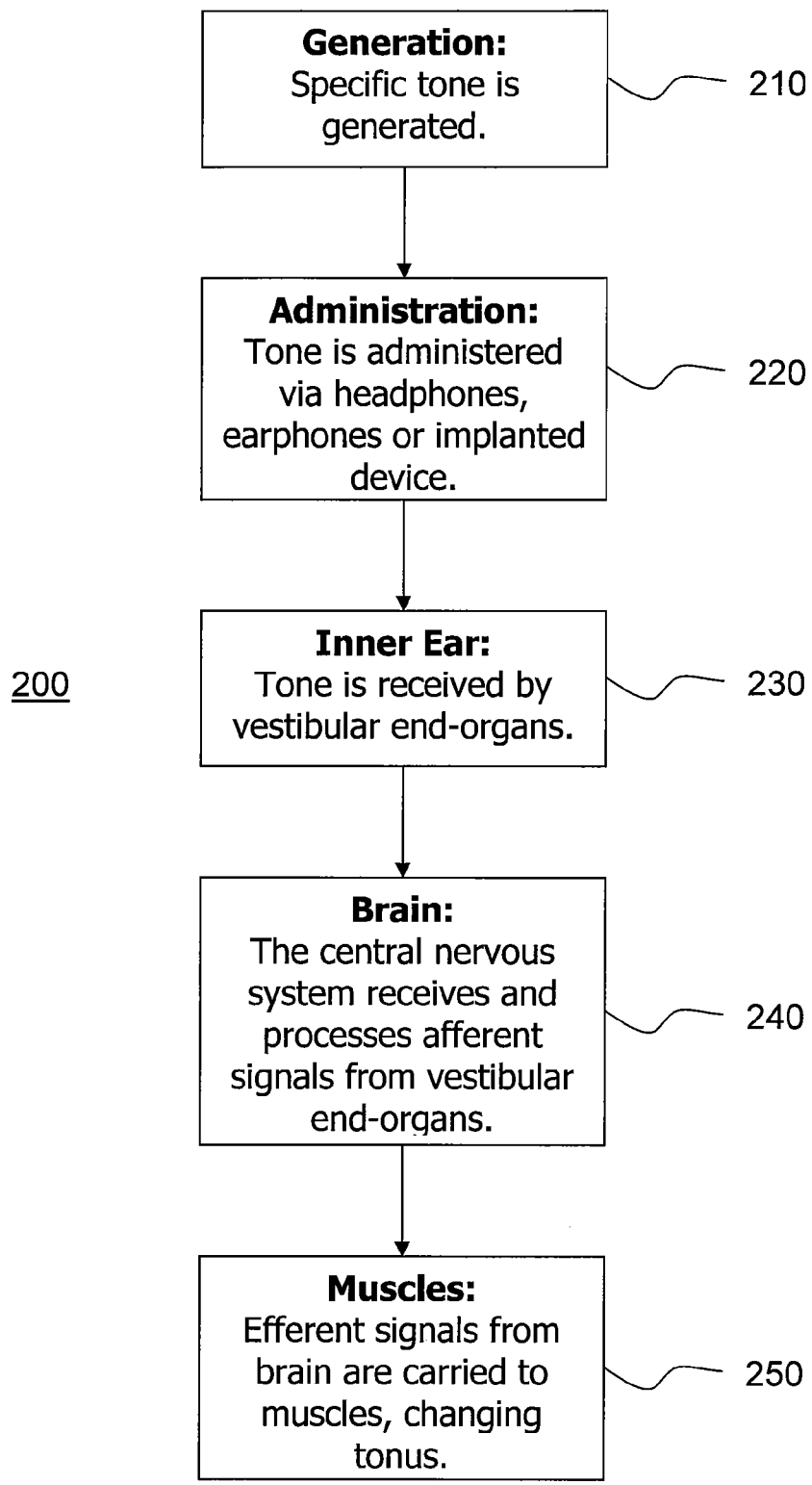
FIG. 2 depicts a flow diagram of a process useful in understanding the present invention.

FIG. 2 depicts a flow diagram of a process useful in understanding the present invention. Specifically, the flow diagram 200 depicts the impact of the invention on a patient within a therapeutic context.

At step 210, a specific tone is generated. The tone generated at step 210 comprises a single having spectral and amplitude characteristics adapted to stimulate vestibular end-organs of a patient.

At step 220, the generated code is administered to a patient or subject via headphones, earphones or implant device.

At step 230, the administered tone is received by vestibular end-organs within the patient's ear.

At step 240, the central nervous system of the patient's brain receives and processes afferent signals provided by the vestibular end-organs.

At step 250, efferent signals from the brain are provided to various muscles, changing thereby the tonus of the muscles.

Figure 3:
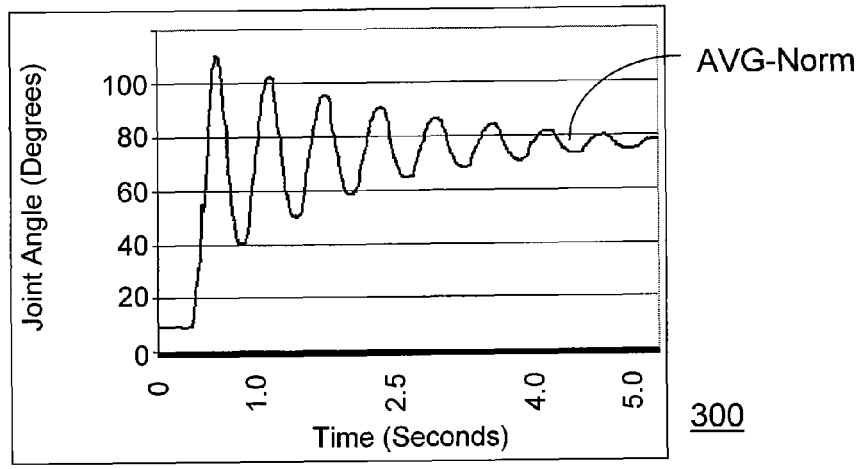
FIGS. 3-5 graphically depicts average range of motion as a function of time for a subjects in a baseline range of motion trial.
Figure 4:
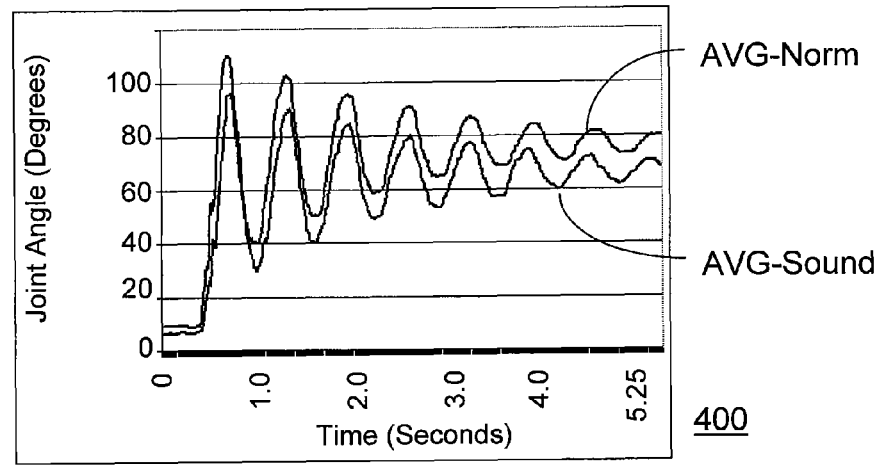
Figure 5:
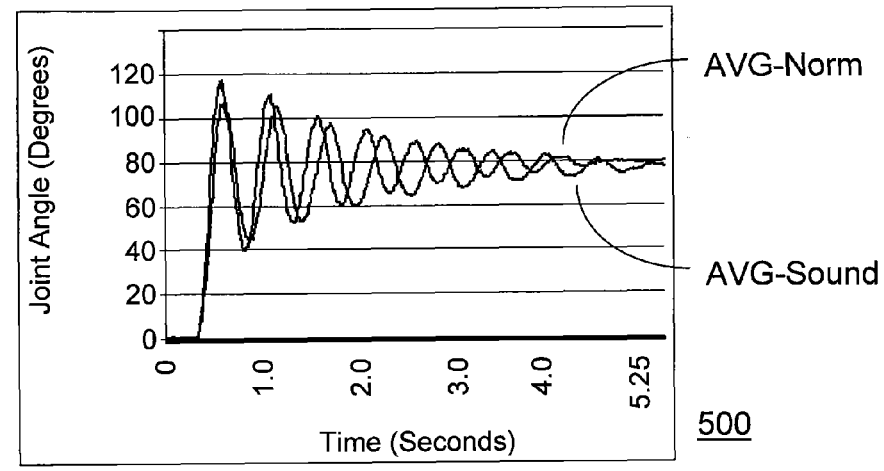

FIGS. 3-5 graphically depicts average range of motion as a function of time for a subjects in a baseline range of motion trial. Specifically, clinical trials were conducted in which an individual's passive lower leg kinematics were quantified before and after acoustic therapy using and apparatus according to an embodiment of the invention. The acoustic therapy was "white-masked" with relaxing natural sounds to make the experience more pleasant. The test parameters were in 4-second phases: Base Frequency: 40 Hz, Modulated By: 40 Hz, Modulation Frequency: 0.2 Hz). Baseline tests were performed before application of the apparatus (FIG. 3), immediately after 15 minutes of application of the apparatus (FIG. 4), and 1½ hours after the 15 minute application of the apparatus (FIG. 5). The results, which display range-of-motion values of the lower leg, are as follows.

Referring to FIG. 3, it can be seen by inspection that a normal or baseline range of motion is depicted.

Referring to FIG. 4, a first curve denoted as AVG-Norm depicts the normal or baseline range of motion, while a second curve denoted as AVG-sound depicts the range of motion immediately following a 15 minute acoustic treatment using the apparatus. It can be seen by inspection that a noticeable kinematic change has occurred (approximately a 15% kinematic change from baseline).

Referring to FIG. 5, a first curve denoted as AVG-Norm depicts the normal or baseline range of motion, while a second curve denoted as AVG-sound depicts the range of motion two hours after a 15 minute acoustic treatment using the apparatus. It can be seen by inspection that normalization of the kinematic change is occurring.

Figure 6:
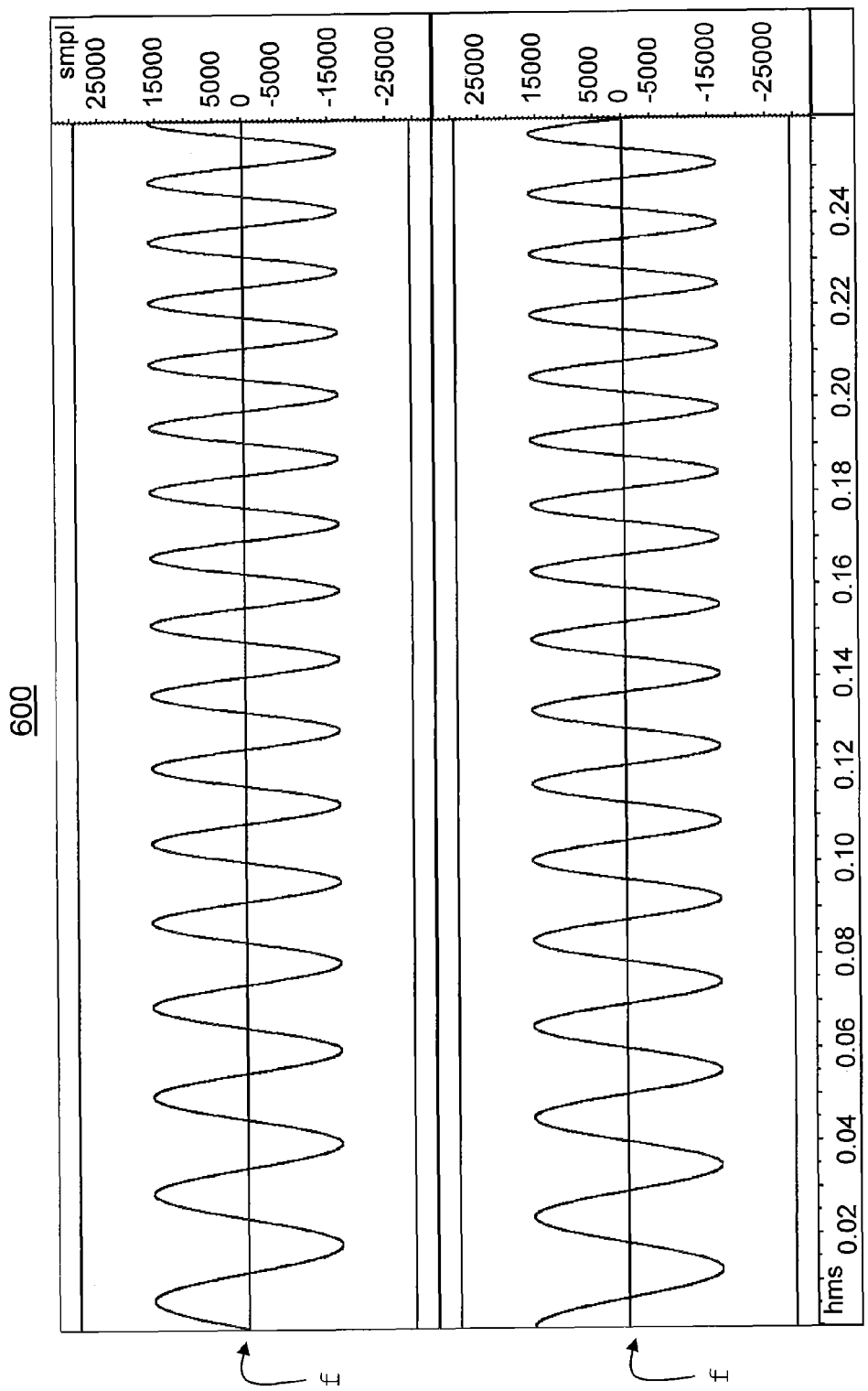
FIG. 6 graphically depicts time domain component signals according to one embodiment.

FIG. 6 graphically depicts time domain component signals according to one embodiment. Specifically, FIG. 6 depicts gain/amplitude as a function of time for two waveforms; namely, a first waveform f1 comprising a 40 Hz sinusoidal signal modulated according to a 0.2 Hz signal, and a second waveform f2 comprising a 40 Hz sinusoidal signal modulated according to the 0.2 Hz signal. It is noted that the first f1 and second f2 modulated sinusoidal signals are out of phase with respect to each other by 90°. In and embodiment core spun into the waveforms of FIG. 6, each of the first $f_1$ and second $f_2$ signals discussed above with respect to FIG. 1 are initially modulated by a signal $f_3$, illustratively a 0.2 Hz signal.

Figure 7:
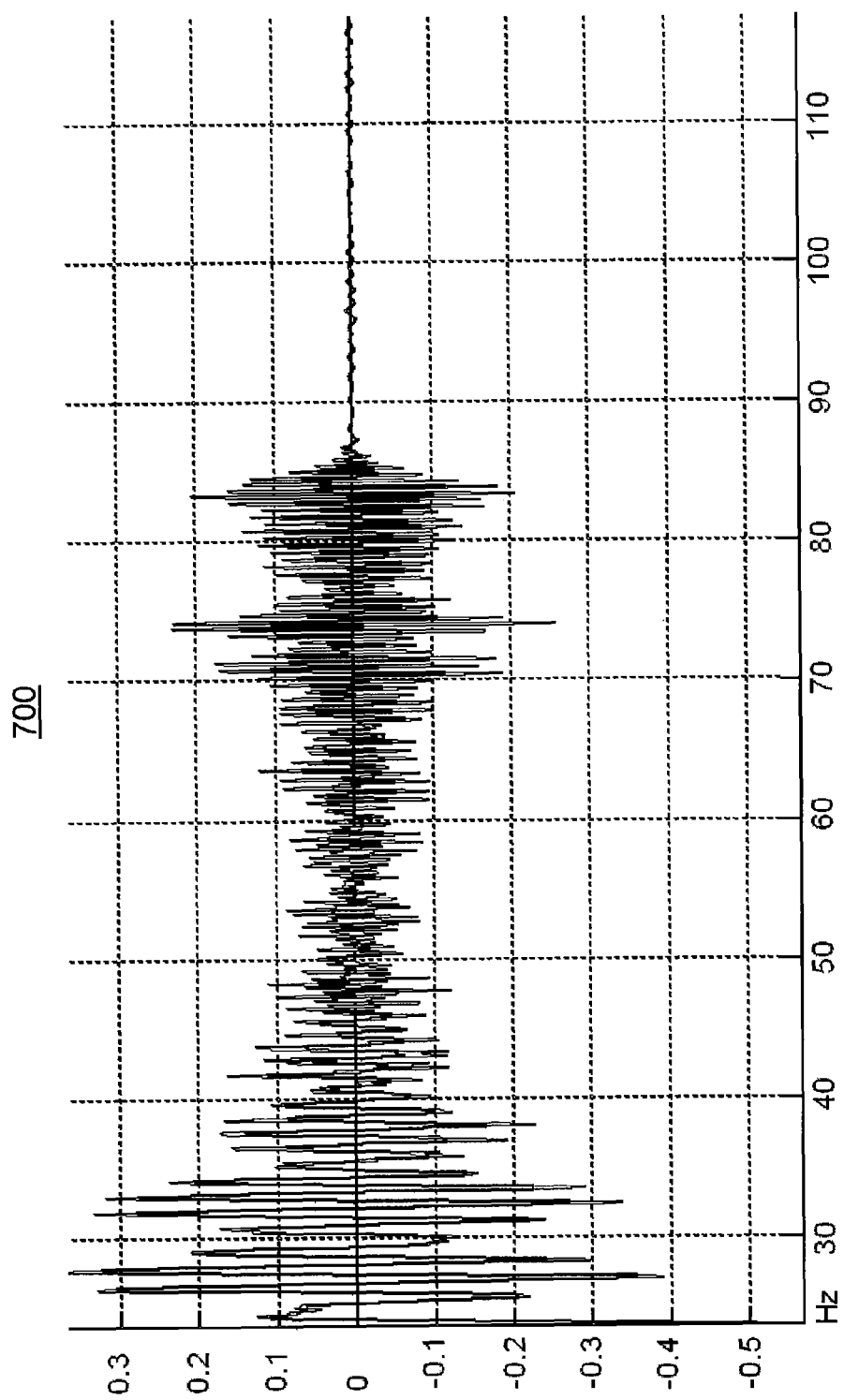
FIG. 7 graphically depicts frequency domain component signals according to one embodiment.

FIG. 7 graphically depicts frequency domain component signals according to one embodiment. Specifically, FIG. 7 depicts spectral energy levels as a function of time for a waveform generated according to one embodiment of the invention. It can be seen that the largest energy levels are at 40 Hz and 80 Hz, with reduced energy levels elsewhere.

The various embodiments of the invention may be implemented within the context of methods, computer readable media and computer program processes. Generally speaking, methods according to the invention may be implemented using computing devices having a processor as well as memory for storing various control programs, other programs and data. The memory may also store an operating system supporting the programs. The processor cooperates with conventional support circuitry such as power supplies, clock circuits, cache memory and the like as well as circuits that assist in executing the software routines stored in the memory. As such, it is contemplated that some of the steps discussed herein as software processes may be implemented within hardware, for example as circuitry that cooperates with the processor to perform various steps. Input/output (I/O) circuitry forms an interface between the various functional elements communicating with the device.

A computing device is contemplated as, illustratively, a general purpose computer that is programmed to perform various control functions in accordance with the present invention, the invention can be implemented in hardware as, for example, an application specific integrated circuit (ASIC) or field programmable gate array (FPGA). As such, the process steps described herein are intended to be broadly interpreted as being equivalently performed by software, hardware or a combination thereof.

The invention may also be implemented as a computer program product wherein computer instructions, when processed by a computer, adapt the operation of the computer such that the methods and/or techniques of the present invention are invoked or otherwise provided. Instructions for invoking the inventive methods may be stored in fixed or removable media, transmitted via a data stream in a signal bearing medium such as a broadcast medium, and/or stored within a working memory within a computing device operating according to the instructions.

As a biomedical device used therapeutically, embodiments of the invention noninvasively stimulate vestibular end-organs in such a manner that alters muscle tonus. As a general consumer product, embodiments of the invention find are useful within the context of a relaxation device. Embodiments of the invention are also useful within the context of vestibular system rehabilitation and neuromuscular reeducation.

One embodiment of the invention comprises a method including the steps of generating a first signal having an approximate frequency between 4 Hz and 90 Hz; frequency modulating the first signal in accordance with a second signal having an approximate frequency between 20 Hz and 60 Hz; and amplitude modulating the frequency modulated signal produce a signal adapted to stimulate vestibular end-organs in a human. In another embodiment, a third signal having an approximate frequency between 0.1 and 10 Hz is mixed with the first and second signals. Vestibular end-organs are stimulated by a mechanical vibration delivered to a human via vibratory apparatus mechanical contact with the human skull, a mechanical vibration delivered to a human via vibratory apparatus communicating with the human mastoid process, a mechanical vibration delivered to a human via whole body vertical oscillation and/or an electrical stimulation signal delivered to one of an implanted delivery device or external delivery device adapted for delivering frequency and amplitude appropriate perturbations to the vestibular system.

One embodiment of the invention comprises an apparatus including a mixer, for mixing a first signal having an approximate frequency between 4 Hz and 90 Hz and a second signal having an approximate frequency between 20 Hz and 60 Hz to produce a mixed signal; an amplifier, for amplitude modulating the mixed signal to produce a signal adapted to stimulate vestibular end-organs in a human; and a delivery device, for stimulating a vestibular end-organs in a human in accordance with the amplitude modulated mixed signal. In one embodiment, the apparatus also includes a controller, for accepting user input/feedback and responsively modifying the frequency of at least one of the first and second signal. The controller may also accept user input and responsively modify the amplitude modulation imparted to the mixed signal by the amplifier. In one embodiment, the mixer also mixes a third signal approximate frequency between 0.1 Hz and 10 Hz with the first and second signals. The delivery device may comprises an audio system adapted to stimulate vestibular end-organs using audio speakers, a mechanical system adapted to stimulate vestibular end-organs using a vibratory apparatus mechanical communication with the human skull, a whole body vertical oscillation device, an implanted or external electrical stimulation device and so on.

While the foregoing is directed to various embodiments of the present invention, other and further embodiments of the invention may be devised without departing from the basic scope thereof. As such, the appropriate scope of the invention is to be determined according to the claims, which follow.

What is claimed is:

1. A method, comprising:
    generating a first signal having an approximate frequency between 4 Hz and 90 Hz;
    frequency modulating the first signal in accordance with a second signal having an approximate frequency between 20 Hz and 60 Hz; and
    amplitude modulating the frequency modulated signal produce a signal adapted to stimulate vestibular end-organs in a human.

2. The method of claim 1, further comprising:
    delivering to a human the signal adapted to stimulate vestibular end-organs.

3. The method of claim 2, wherein the signal adapted to stimulate vestibular end-organs comprises an audio signal delivered to a human via audio speakers.

4. The method of claim 1, further comprising:
    frequency modulating the first signal in accordance with a third signal having an approximate frequency between 0.1 and 10 Hz.

5. The method of claim 1, further comprising:
    frequency modulating the first signal in accordance with a third signal having an approximate frequency of 0.2 Hz.

6. The method of claim 1, wherein the signal adapted to stimulate vestibular end-organs comprises a mechanical vibration delivered to a human via vibratory apparatus mechanical contact with the human skull.

7. The method of claim 1, wherein the signal adapted to stimulate vestibular end-organs comprises a mechanical vibration delivered to a human via vibratory apparatus communicating with the human mastoid process.

8. The method of claim 1, wherein the signal adapted to stimulate vestibular end-organs comprises a mechanical vibration delivered to a human via whole body vertical oscillation.

9. The method of claim 1, wherein the signal adapted to stimulate vestibular end-organs comprises an electrical stimulation signal delivered to one of an implanted delivery device or external delivery device adapted for delivering frequency and amplitude appropriate perturbations to the vestibular system.

10. Apparatus, comprising:
    means for generating a first signal having an approximate frequency between 4 Hz and 90 Hz;
    means for frequency modulating the first signal in accordance with a second signal having an approximate frequency between 20 Hz and 60 Hz;
    means for accepting user input and responsively modifying the frequency of at least one of the first and second signal; and
    means for amplitude modulating the frequency modulated signal produce a signal adapted to stimulate vestibular end-organs in a human.

11. Apparatus, comprising:
    a mixer, for mixing a first signal having an approximate frequency between 4 Hz and 90 Hz and a second signal having an approximate frequency between 20 Hz and 60 Hz to produce a mixed signal;
    an amplifier, for amplitude modulating the mixed signal to produce a signal adapted to stimulate vestibular end-organs in a human;
    a controller, for accepting user input and responsively modifying the frequency of at least one of the first and second signal; and
    a delivery device, for stimulating a vestibular end-organs in a human in accordance with the amplitude modulated mixed signal.

12. The apparatus of claim 11, wherein:
    a controller, for accepting user input and responsively modifying the amplitude modulation imparted to the mixed signal by the amplifier.

13. The apparatus of claim 11, wherein:
    the mixer also mixes a third signal approximate frequency between 0.1 Hz and 10 Hz with the first and second signals.

14. The apparatus of claim 11, wherein the delivery device comprises an audio system adapted to stimulate vestibular end-organs using audio speakers.

15. The apparatus of claim 11, wherein the delivery device comprises a mechanical system adapted to stimulate vestibular end-organs using a vibratory apparatus mechanical communication with the human skull.

16. The apparatus of claim 11, wherein the delivery device comprises a whole body vertical oscillation device.

17. The apparatus of claim 11, wherein the delivery device comprises one of an implanted or external electrical stimulation device.

* * * * *